US00PP15863P3

(12) United States Plant Patent

Rowe et al.

(10) Patent No.: US PP15,863 P3
(45) Date of Patent: Jul. 12, 2005

(54) DESSERT BANANA PLANT NAMED 'FHIA-26'

(50) Latin Name: *M. acuminata×balbisiana*
Varietal Denomination: FHIA-26

(75) Inventors: Phillip Ray Rowe, deceased, late of La Lima (HN); by Mark Rowe, legal representative, Austin, TX (US)

(73) Assignee: Fundación Hondurefia de Investigación Agricola, San Pedro Sula (HN)

( * ) Notice: Subject to any disclaimer, the term of this patent is extended or adjusted under 35 U.S.C. 154(b) by 144 days.

(21) Appl. No.: 10/703,128

(22) Filed: Nov. 6, 2003

(65) Prior Publication Data

US 2005/0114957 P1 May 26, 2005

(51) Int. Cl.[7] ..... A01H 5/00
(52) U.S. Cl. ..... Plt./160
(58) Field of Search ..... Plt./160

(56) References Cited

U.S. PATENT DOCUMENTS

| | | | |
|---|---|---|---|
| PP8,983 | P | 11/1994 | Rowe |
| PP9,791 | P | 2/1997 | Rowe |
| PP13,874 | P3 | 6/2003 | Rowe |

OTHER PUBLICATIONS

International Network for the Improvement of Banana and Plantain (INIBAP) [online]. Annual Report 1998 [retrieved 1999]. Retrieved from the Internet: <http://www.inibap.org/>. pp. 1–3, 16–25.*

International Network for the Improvement of Banana and Plantain (INIBAP) [online]. Annual Report 1999 [retrieved 2000] Retrieved from the Internet: <http;//www.inibap, org/>. pp. 1–3, 21–27.*

* cited by examiner

*Primary Examiner*—Anne Marie Grunberg
*Assistant Examiner*—June Hwu
(74) *Attorney, Agent, or Firm*—Garvey, Smith, Nehrbass & Doody, L.L.C.; Seth M. Nehrbass

(57) ABSTRACT

This new and distinct variety of hybrid dessert banana plant has both *Musa acuminata* and *Musa balbisiana* in its pedigree. Its Latin name is *Musa acuminata×balbisiana* group AABB. AA representing two genomes of *M. acuminata* and BB representing two genomes of *M. balbisiana*. It has the following unique combination of desirable features:

1. A high level of resistance to *Mycosphaerella fijiensis*, causal fungus of the black Sigatoka (black leaf streak) disease.
2. A tall plant height.
3. A strong root system that makes it a hardy plant resistant to strong winds or weevil attach (corm borer *Cosmopolites sordidus*).
4. Fruit bunch sizes that are frequently greater than 20 kg.
5. Ripe fruit has a very good taste, flavor and texture.

2 Drawing Sheets

Latin name of the genus and species of the plant claimed: This tetraploid plant has both *Musa acuminata* and *Musa balbisiana* in its pedigree. This tetraploid hybrid is the product of an inter-specific cross between a triploid cultivar (ABB) type 'Bluggoe' and an improved diploid (AA) of *M. acuminata*. Its Latin name is *M. acuminata×balbisiana* group AABB. AA representing two genomes of *M. acuminata* and BB representing two genomes of *M. balbisiana*.

Variety denomination: 'FHIA-26'.

BACKGROUND OF THE INVENTION

This new hybrid was developed at FHIA in La Lima, Cortés, Honduras from a field cross made in 1996. It was selected in 1998 from several first-generation seedlings from the cross 'Pisang Awak'×SH-3437 (both unpatented). 'Pisang Awak' is a naturally occurring, sweet-flavored, triploid clone that is grown commercially on a small scale in India and Cuba. SH-3437, which was developed by the inventor, is an improved diploid that is resistant to *Mycosphaerella fijiensis*, causal fungus of the black Sigatoka (black leaf streak) disease. SH-3437 was derived by crossing two bred diploids, SH-2989 and SH-3217. SH-2989 is a bred diploid derived from the cross of the bred diploid SH-2752 and Calcutta IV, a wild *M. acuminata* subsp. *burmanica* accession from Burma. The SH-3217 parent of SH-3437 is a complex bred diploid, which has in its pedigree the parthenocarpic 'Guyod', natural diploids 'Tjau Lagada' and 'Sinwobogi', and a wild *M. acuminata* subsp. *malaccensis* accession, from the Philippines, Java, Irian Jaya and Malaysia, respectively. 'FHIA-26' was selected as a tetraploid hybrid that maintained the fruit characteristics and resistance to *Mycosphaerella fijiensis* of its triploid parental line, but differs from 'Pisang Awak' in higher fruit yields and less female fertility. (This trait of female fertility makes the practice of elimination of male flowers necessary as a cultivation practice.) This new hybrid dessert banana plant was asexually reproduced by corms by the inventor in the Centro Experimental Demostrativo Phillip Ray Rowe, the experimental farm of FHIA in La Lima, Cortés, Honduras, and shown that all plant and fruit characteristics run true to the original selected plant and are identical in all aspects.

BRIEF SUMMARY OF THE INVENTION

This new and distinct hybrid variety of dessert banana is a vigorous, tall plant that produces large bunches of fruit. It is highly resistant to *Mycosphaerella fijiensis*, causal fungus of the black Sigatoka (black leaf streak) disease, the most destructive and most costly to control disease of bananas and plantains worldwide. Interest in this new variety is as a new specialty banana with excellent taste, texture and flavor that can complement the 'Cavendish' dessert bananas in the U.S., European and Japanese markets.

BRIEF DESCRIPTION OF THE PHOTOGRAPHS

The accompanying photographic reproductions show typical specimens of the new hybrid dessert banana variety:

BRIEF DESCRIPTION OF HOW THE NEW VARIETY IS DISTINGUISHED

FROM ITS MALE PARENT AND RELATED KNOWN CULTIVAR

Figure 1:
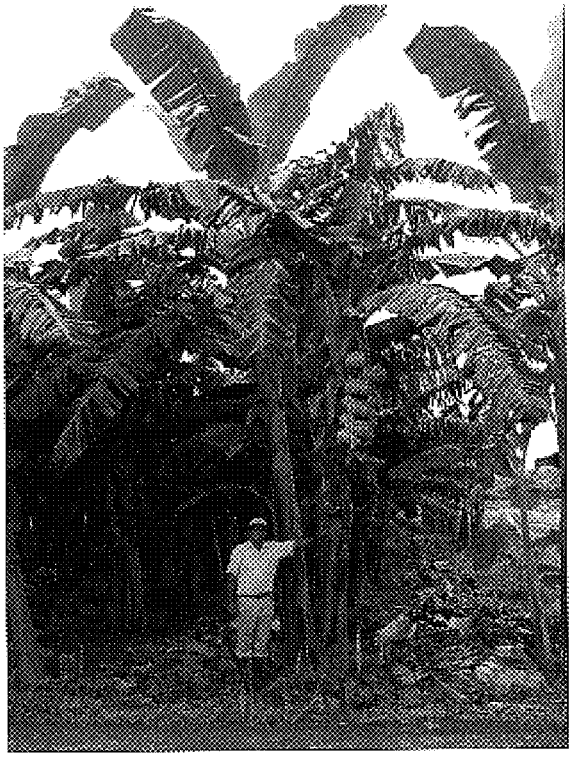
FIG. 1 shows a typical 'FHIA-26' banana plant and a fruit bunch one month before harvesting.
Figure 2:
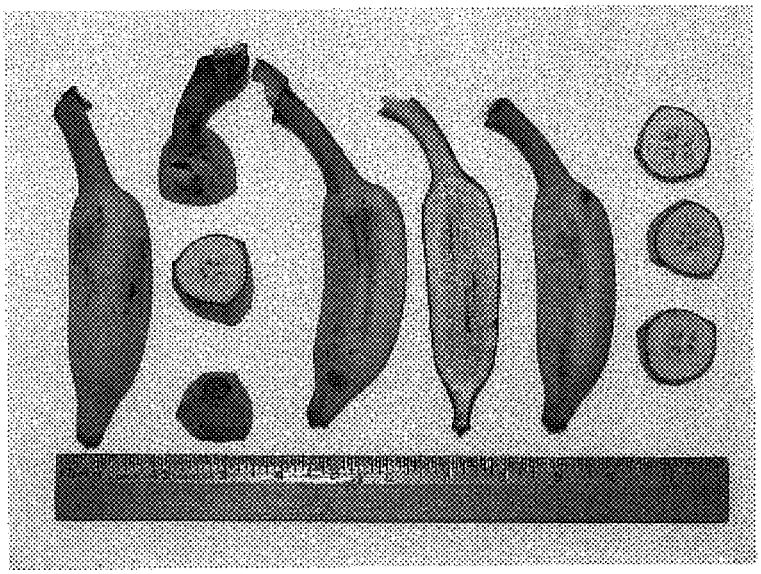
FIG. 2 shows representative whole fingers, and longitudinal- and cross-sections of fruit at harvest stage of the new variety.
Figure 3:
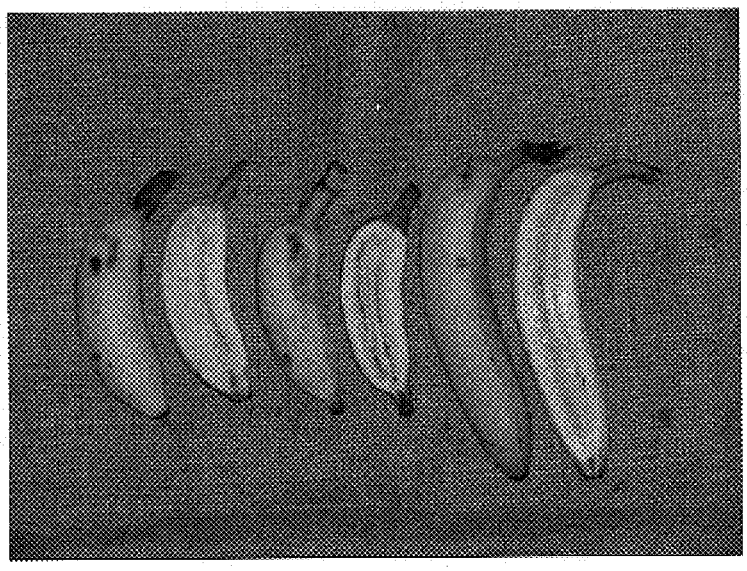
FIG. 3 shows a comparison of fingers of 'FHIA-26' (center) with the varieties 'Cavendish' (right) and 'silk' (left).
Figure 4:
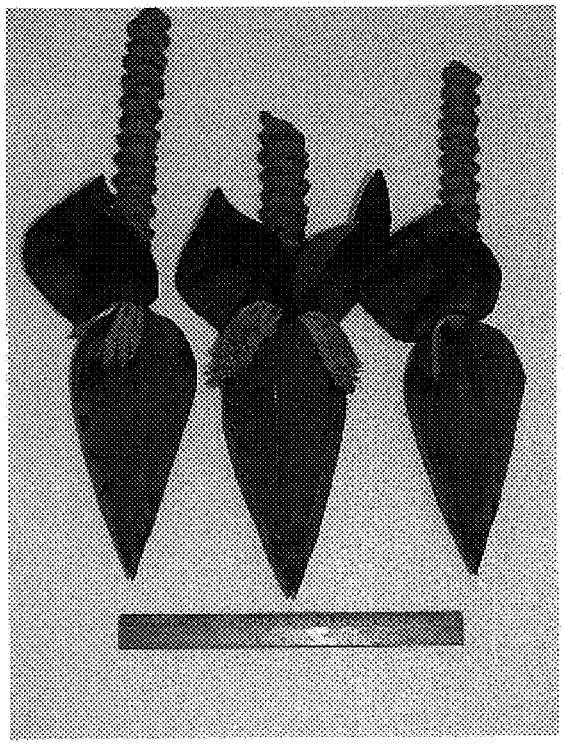
FIG. 4 shows three male buds of 'FHIA-26', the inside and outside surface color of bracts are red (43-C) and greyed puple (183 D), respectively.

The tetraploid, hybrid banana plant 'FHIA-26' (4N), type AABB, is differentiated from its progenitors primarily in the level of ploidy; the female parent, 'Pisang Awak', is a triploid (3N), type ABB, and the male parent, SH 3437, is a diploid (2N), type AA. The raceme and individual fruits of the diploid hybrid SH-3437 are completely different from those of 'Pisang Awak' and 'FHIA-26'. The width or diameter of the FHIA-26 raceme is greater than that of the Pisang Awak raceme. 'FHIA-26' has less fingers per hand than Pisang Awak and the individual fruit of 'FHIA-26' is longer and has a greater diameter than the fruit of 'Pisang Awak'. The peel thickness of green and mature 'FHIA-26' fruit is greater than that of 'Pisang Awak'. The percent soluble solids (measured as grades of Brix) of Pisang Awak and 'FHIA-26' are greater than the average Brix score of 20 in maturity grade 6 reported for the varieties in the Cavendish banana group (Grand Nain, Valery and Williams). 'Pisang Awak' has an average Brix score of 28 compared to a Brix score of 26 for 'FHIA-26'.

DETAILED BOTANICAL DESCRIPTION

The following is a detailed botanical description of the new and distinct variety of hybrid dessert banana plant, which includes its general appearance, pseudostem and suckers, petiole, midrib, leaf, inflorescence and male bud, flower bract, male flower, and fruit. This description is based on observations of specimens grown in the FHIA experimental farm near La Lima, Cortés, Honduras. The 140 plant descriptors presented herein are in accordance with and include all of the 117 international standards found in "Descriptors for Banana (*Musa* spp.)" elaborated by CIRAD/INIBAP/IPGRI. The color terminology is in accordance with The U.K.'s Royal Horticultural Society's Colour Chart, 2001.

Plant general appearance:

*Ploidy.*—Tetraploid (AABB).

*Leaf habit.*—Drooping.

Pseudostems/suckers: (Data taken 450 days after transplanting at first ripe fruit.)

*Pseudostem height.*—3.50–4.30 m.

*Pseudostem appearance.*—Robust.

*Pseudostem color.*—Yellow-Green (144-B).

*Pseudostem appearance.*—Dull (waxy).

*Predominant underlying color of the pseudostem.*—Yellow-Green (145-A).

*Pigmentation of the underlying pseudostem.*—Purple (N 77-B).

*Sap colour.*—Tending toward Milky (202-D).

*Wax on leaf sheaths.*—Very waxy.

*Number of suckers.*—4.

*Size of suckers at harvest of the parent plant.*—2.30 to 3.10 m in height.

*Position of suckers.*—Close to parent (vertical growth).

Petioles/midribs/leaves: (Data taken on the 3$^{rd}$ fully unfolded leaf counting down from the top of the plant at 430 days—time of harvest—after transplanting).

*Blotches at the petiole base.*—Small blotches.

*Color of blotches.*—Brown (N 200-C).

*Petiole canal of leaf three.*—Margins curved inward.

*Petiole margins.*—Winged and clasping the pseudostem.

*Wing appearance.*—Dry.

*Wing color.*—Gray-Brown (199-D).

*Petiole margin color.*—Green (141-D).

*Edge of petiole margin.*—Colorless.

*Petiole margin width.*—8 to 10 mm.

*Leaf blade length.*—221 to 260 cm.

*Leaf blade width.*—81 to 90 cm.

*Petiole length.*—51 to 70 cm.

*Color of upper leaf surface.*—Green (137-A).

*Appearance of upper leaf surface.*—Tending to Shiny.

*Color of lower leaf surface.*—Green (138-B).

*Appearance of lower leaf surface.*—Dull.

*Wax on leaves.*—Very waxy.

*Insertion point of leaf blades on petiole.*—Mostly symmetric.

*Shape of leaf blade base.*—Both sides tapered in first leaves going to both rounded in later leaves.

*Leaf corrugation.*—Few stripes.

*Color of midrib dorsal surface.*—Green (138-B).

*Color of midrib ventral surface.*—Yellow-Green (146-D).

*Color of cigar leaf dorsal surface.*—Green (143-C).

*Blotches on leaves of water suckers.*—Without blotches.

Inflorescence/male bud: (Data taken 330 days after transplanting at completion of flower emergence.)

*Peduncle length.*—65 to 70 cm.

*Empty nodes on peduncle.*—Two or more.

*Peduncle width.*—6.5–7.5 cm.

*Peduncle color.*—Yellow-Green (144-A).

*Peduncle hairiness.*—Hairless.

*Bunch position.*—Slightly angled.

*Bunch shape.*—Cylindrical.

*Bunch appearance.*—Very compact.

*Flowers that form the fruit.*—Female.

*Fruits.*—Biseriate.

*Rachis type.*—Present and male bud may be degenerated or persistent.

*Rachis position.*—Falling vertically.

*Rachis appearance.*—Bare.

*Average length of rachis.*—1.51 m.
*Male bud type.*—Normal (present).
*Male bud shape.*—Ovoid.
*Male bud size.*—21 to 30 cm.
*Average diameter of male bud.*—11.4 cm.

Bract: (Data taken 330 days after transplanting at completion of flower emergence.)
*Bract base shape.*—Large shoulder.
*Bract base size.*—Average 6 cm for the part connected to the rachis.
*Bract apex shape.*—Obtuse.
*Bract imbrications.*—Young bracts slightly overlap at apex of bud.
*Bract length.*—Average 26.5 cm at longest point.
*Bract width.*—Average 20 cm at widest point.
*Color of the bract external face.*—Grayed-Purple (183-D).
*Color of the bract internal face.*—Red (43-C).
*Color on the bract apex.*—Tinted with yellow (4-B).
*Color stripes on bract.*—Without discolored lines (not ridges) on the external face.
*Bract scars on rachis.*—Very prominent.
*Fading of color on bract base.*—Color homogenous.
*Male bract shape.*—ovate.
*Male bract lifting.*—Lifting one or two at a time.
*Bract behavior before falling.*—Revolute (rolling).
*Wax on the bract.*—Moderately waxy.
*Presence of grooves on the bract.*—Moderate.

Male flowers: (Data taken 330 days after transplanting at completion of flower emergence).
*Male flower behavior.*—Falling before the bract.
*Compound tepal basic color.*—Red-Purple (65-A).
*Compound tepal pigmentation.*—Very few or no visible sign of pigmentation.
*Lobe color of compound tepal.*—Yellow (13-B).
*Lobe development of compound tepal.*—Developed.
*Free tepal color.*—Opaque white (155-A).
*Free tepal shape.*—Oval.
*Free tepal appearance.*—More or less smooth.
*Free tepal apex development.*—Developed.
*Free tepal apex shape.*—Filiform.
*Average length of free tepals.*—30 mm.
*Average length of compound tepal.*—66 mm.
*Average length of the style.*—78 mm.
*Average length of filament.*—44 mm.
*Anther exsertion.*—10 mm.
*Filament color.*—White (155-A).
*Anther color.*—Yellow-White (158-A).
*Pollen sacs color.*—Red-Purple (58-D).
*Pollen vitality.*—Medium.
*Style basic color.*—White (155-C).
*Pigmentation on style.*—Without pigmentation.
*Style exsertion.*—5 mm.
*Style shape.*—Straight.
*Stigma color.*—Yellow-Orange (14-D).
*Ovary shape.*—Slightly arched.
*Ovary basic color.*—White (155-A).
*Ovary pigmentation.*—Very few or no visible signs of pigmentation.
*Average length of ovary of female flower.*—5 cm.
*Dominant color of male flower.*—Red-Purple (65-A).
*Irregular flowers.*—Absent.
*Arrangement of ovules.*—Two-rowed.

Fruit: (Data taken at 480 days from transplanting at harvest).
*Fruit position.*—Curved upward.
*Number of fruits per hand.*—16 average.
*Fruit length.*—13–18 cm.
*Fruit diameter.*—33.8–37.5 mm.
*Fruit shape* (*longitudinal curvature*).—Straight (or slightly curved).
*Transverse section of fruit.*—Slightly ridged.
*Fruit apex.*—Bottle-necked.
*Remains of flower relicts at fruit apex.*—Persistent style.
*Fruit pedicel length.*—40 mm.
*Fruit pedicel width.*—14 mm.
*Pedicel surface.*—Hairless.
*Fusion of pedicels.*—Very partially or no visible sign of fusion.
*Immature fruit peel color.*—Green (143-C).
*Mature fruit peel color.*—Yellow-Orange (14-C).
*Fruit peel thickness.*—2.0 mm.
*Adherence of the fruit peel.*—Fruit peels easily.
*Cracks in fruit peel.*—Without cracks.
*Pulp in fruit.*—With pulp.
*Pulp color before maturity.*—White (155-D).
*Pulp color at maturity.*—White (155-D).
*Fruits fall from hands.*—Persistent.
*Fruit is eaten.*—Rripe.
*Flesh texture.*—Firm.
*Predominant taste.*—Sweet and acidic (apple like).
*Main use.*—Dessert banana.
*Presence of seed with source of pollen.*—5 to 20.
*Seed surface.*—Wrinkled.
*Seed shape.*—Rounded (but not completely spherical).

Agronomic characteristics (averages taken during 1998–1999 for first crop in a plot of 10 plants with no control of diseases):
*Days from planting to first flowering.*—325.
*Number of leaves at flowering.*—13.
*Number of functional leaves* (*less than 15% of area necrotic*) *at flowering.*—13.
*Number of leaves at harvest.*—10.
*Number of functional leaves* (*less than 15% of area necrotic at harvest*).—9.
*Days from flowering until harvest.*—150.
*Bunch weight.*—24.5 kg.
*Number of hands.*—9.
*Finger length.*—16 cm.
*Number of fingers per bunch.*—143.
*Days from first flowering until second flowering.*—250.

This hybrid dessert banana and its fruit described above may vary slightly in detail due to cultural practices, soil types and climatic conditions under which the variety may be grown; the present description is that of the variety grown under the ecological conditions prevailing on the FHIA experimental station near La Lima, Cortés, Honduras.

It is claimed:

1. A new and distinct hybrid variety of dessert banana plant, substantially as illustrated and described, which is a tall plant and has a high level of resistance to *Mycosphaerella fijiensis*, causal fungus of the black Sigatoka (black leaf streak) disease; the fresh ripe fruit is further characterized by having a very good taste, flavor and texture.

* * * * *